United States Patent

Terni et al.

Patent Number: 5,869,484
Date of Patent: Feb. 9, 1999

[54] PHENYLCARBAMATE DERIVATIVES SUITABLE TO THE USE AS ANTICHOLINESTERASE SUBSTANCES

[75] Inventors: Patrizia Terni, Milan; Lucia Mairani, Lonate Pozzolo; Giacomina Mandelli, Sesto San Giovanni; Pier Giuseppe Pagella, Isola Sant'Antonio; Donata Marchesini; Stefano Maiorana, both of Milan; Mario Brufani, Castel Gandolfo, all of Italy

[73] Assignee: Mediolanum Farmaceutici S.P.A., Milan, Italy

[21] Appl. No.: 776,052

[22] PCT Filed: Jul. 13, 1995

[86] PCT No.: PCT/EP95/02752

§ 371 Date: Jan. 17, 1997

§ 102(e) Date: Jan. 17, 1997

[87] PCT Pub. No.: WO96/02524

PCT Pub. Date: Feb. 1, 1996

[30] Foreign Application Priority Data

Jul. 18, 1994 [IT] Italy .................. MI94A1494

[51] Int. Cl.⁶ ............... A61K 31/535; C07D 265/32; C07D 413/00; C07D 265/30
[52] U.S. Cl. .................. 514/231.2; 514/231.5; 514/231.8; 514/235.5; 514/235.8; 514/237.8; 514/239.2; 514/239.5; 544/87; 544/121; 544/128; 544/130; 544/162; 544/164; 544/168
[58] Field of Search ............ 544/162, 164, 544/168, 87, 130, 121, 128; 514/231.2, 231.5, 231.8, 235.5, 235.8, 237.8, 239.2, 239.5

[56] References Cited

FOREIGN PATENT DOCUMENTS

| | | |
|---|---|---|
| 0154864A1 | 2/1985 | European Pat. Off. . |
| 0193926 A2 | 4/1986 | European Pat. Off. . |
| 0575954 A1 | 6/1993 | European Pat. Off. . |
| WO 92/00072 | 1/1992 | WIPO . |

OTHER PUBLICATIONS

Podyani;Acta Pharm. Hung. (1992), 62(5), 218–24, 1992.
"Heterocycles", vol. 110, 1989, p. 673.
Davies, Robert E., et al: "Investigations on the Influence of Chemical Constitution upon Toxicity", Part III., pp. 191–196, 1947.
Chemical Abstracts Service, Registry Handbook, Number Section, 1977 Supplement, Registry Numbers 63306–25–2 through 65229–05–2.

Primary Examiner—Mukund J. Shah
Assistant Examiner—Bruck Kifle
Attorney, Agent, or Firm—McDermott, Will & Emery

[57] ABSTRACT

Phenylcarbamate derivatives suitable to the use as anticholinesterase substances having the general formula (I)

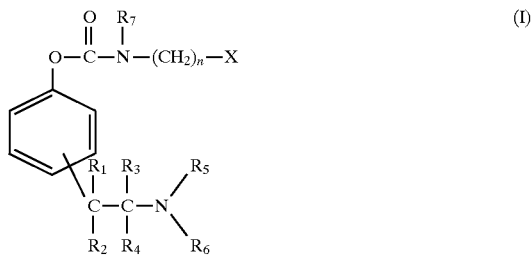

wherein the meaning of $R_1$–$R_7$ and X substituentes together with n will be defined in the text.

15 Claims, No Drawings

PHENYLCARBAMATE DERIVATIVES SUITABLE TO THE USE AS ANTICHOLINESTERASE SUBSTANCES

PRIOR ART

Various memory disorders and particularly the senile dementia of Alzheimer kind are characterized by a reduction in some cerebral areas of the acetylcholine neurotransmitter levels. In these situations the acetylcholinesterease inhibition, enzyme hydrolizing the acetylcholine, turns out useful for therapeutic aims.

It is known that the physostigmine is a powerful natural inhibitor of the acetylcholinesterase and various clinical studies showed that it gives beneficial results in the treatment of the patients affected by mental pathologies. However the physostigmine has unfavourable pharmacokinetic characteristics and side-effects as to make not very easy its clinical use.

It is also known that eptastigmine or heptylcarbamic ester of the eseroline (EP 0154864), even if it is an acetylcholinesterase inhibitor less powerful "in vitro" than the physostigmine, has with respect to it better pharmacokinetic characteristics and reduced side-effects. Moreover other drugs, such as for example Tacrine (New Engl. J. Med., 315, 1241 (1986)), Velnacrine (U.S. Pat. No. 4,631,286), $RA_7$ (EP 193926), E2020 (EP 296560) are in advanced clinical study for the Alzheimer's disease therapy.

They showed some efficacy but at times together with heavy side-effects too, for example Tacrine and Velnacrine induce high transaminase levels (Eur. Neuropsychopharmacol., 1(3), Abst. S-7-2 (1991)).

Then the search for new substances having activity inhibiting the acetylcholinesterase and low toxicity is more and more topical.

SUMMARY

A new class of anticholinesterase compounds which show a higher activity and side-effects lower than the known compounds and moreover have the advantage to be prepared with a simple and economical process has now been found. Moreover some of them carry on a selective activity on the AChE without modifying the BuChE.

Said class of compounds, derivatives of the phenylcarbamate, has the following general formula

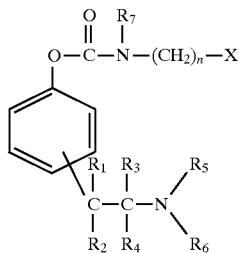

(I)

wherein $R_1$, $R_2$, $R_3$ and $R_4$, equal or different, represent: hydrogen, linear or branched ($C_1$–$C_4$) alkyl, cycloalkyl ($C_3$–$C_6$), aryl ($C_1$–$C_4$) alkyl, hydroxyl, or $R_1$ and $R_2$ together are —$(CH_2)_m$— wherein m is an integer number from 3 to 6 and form a cycle from 3 to 6 carbon atoms;

$R_5$ and $R_6$, equal or different, represent: hydrogen, linear or branched alkyl ($C_1$–$C_6$), aryl ($C_1$–$C_6$) alkyl, acyl or the group:

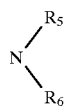

is a radical derivatived from the morpholine, piperidine, tetrahydroquinoline, tetrahydroisoquinoline, alkylpiperazine, arylpiperazine, arylalkylpiperazine, acylpiperazine, the dialkylaminoalkyl group being in para or meta position with respect to the carbamic group;

$R_7$ represents hydrogen or a linear or branched ($C_1$–$C_4$) alkyl;

n is an integer number from 0 to 20;

X is selected from the radicals

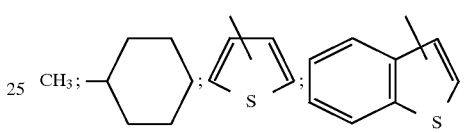

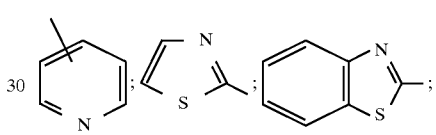

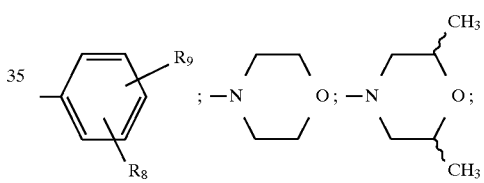

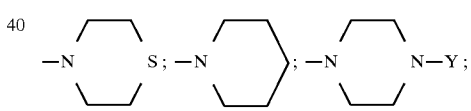

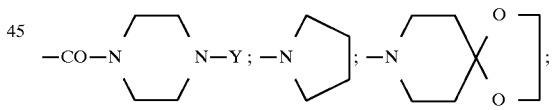

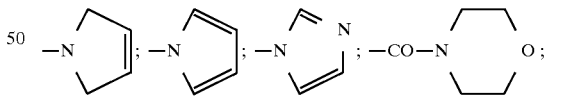

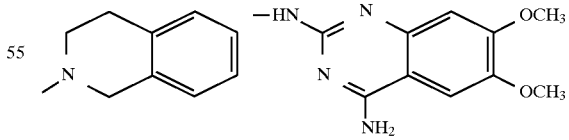

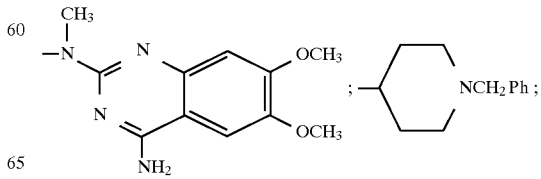

-continued

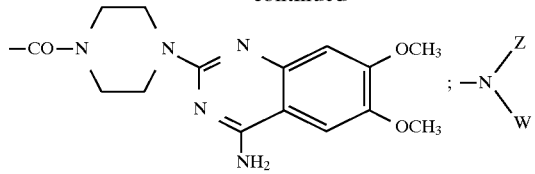

wherein $R_8$ and $R_9$, equal or different, represent: linear or branched ($C_1$–$C_4$) alkyl, halogen, methoxy, nitro, trifluoromethyl;

Y represents a linear or branched ($C_1$–$C_4$) alkyl, acyl, aryl, arylalkyl;

W and Z, equal or different, represent a linear or branched ($C_1$–$C_4$) alkyl, arylalkyl, methoxyethyl, methoxypropyl, methoxybenzyl;

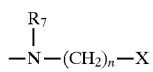

group is an heterocyclic group such as for example

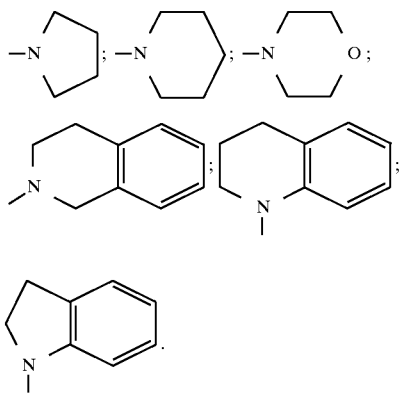

provided that when $R_3=R_4=H$, $R_1$ and $R_2$ cannot both be H, and when $R_7$ is H and n is O, X cannot be methyl.

The compounds having general formula (I) may be salified with pharmacologically acceptable acids selected from the group comprising HCl, HBr, $H_2SO_4$, $H_3PO_4$, $HClO_4$, $CH_3SO_3H$, p-toluenesulfonic acid, citric acid, tartaric acid, maleic acid, salicylic acid, fumaric acid, succinic acid, oxalic acid, and so on.

The compounds of the present invention, due to the anticholinesterase activity may be used in human therapy for the treatment of those pathologies which benefit from an acetylcholine increase such as for example the Alzheimer's disease.

DETAILED DESCRIPTION OF THE INVENTION

The characteristics and the advantages of the phenylcarbamate derivatives for the use as anticholinesterase substances according to the present invention, and also the process for their preparation, will be mainly pointed out in the course of the following detailed description.

The compounds of the present invention have the following general formula:

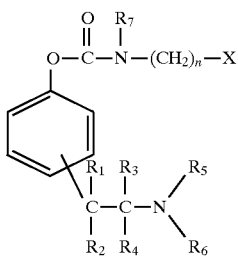

wherein $R_1$, $R_2$, $R_3$ and $R_4$, equal or different, represent: hydrogen, linear or branched ($C_1$–$C_4$) alkyl, cycloalkyl ($C_3$–$C_6$), aryl ($C_1$–$C_4$) alkyl, hydroxyl, or $R_1$ and $R_2$ together are —$(CH_2)_m$— wherein m is an integer number from 2 to 5 and form a cycle from 3 to 6 carbon atoms; $R_5$ and $R_6$, equal or different, represent: hydrogen, linear or branched alkyl ($C_1$–$C_6$), aryl ($C_1$–$C_6$) alkyl, acyl or the group:

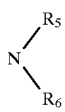

is a radical derived from the morpholine, piperidine, tetrahydroquinoline, tetrahydroisoquinoline, alkylpiperazine, arylpiperazine, arylalkylpiperazine, acylpiperazine, the dialkylaminoalkyl group being in para or meta position with respect to the carbamic group;

$R_7$ represents the hydrogen or a linear or branched ($C_1$–$C_4$) alkyl;

n is an integer number from 0 to 20;

X is selected from the radicals

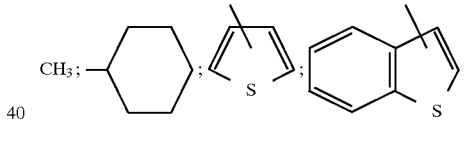

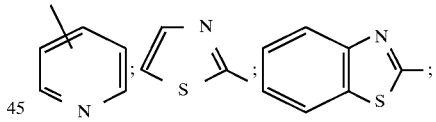

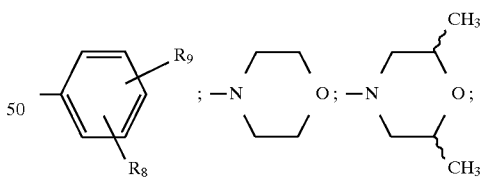

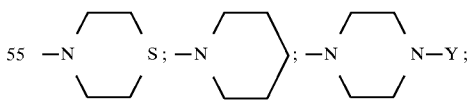

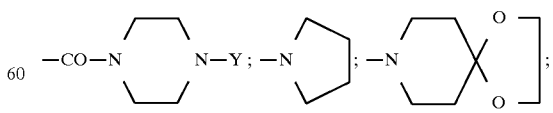

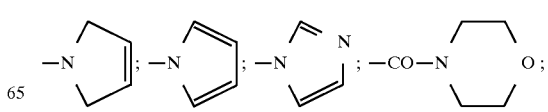

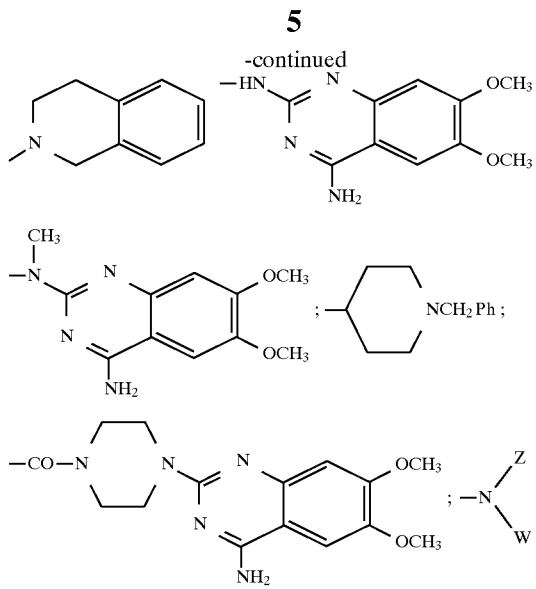

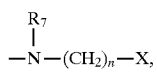

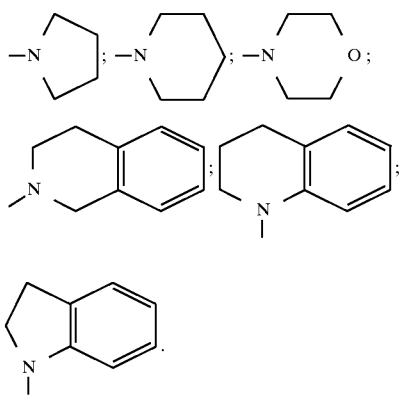

wherein $R_8$ and $R_9$, equal or different, represent: linear or branched ($C_1$–$C_4$) alkyl, halogen, methoxy, nitro, trifluoromethyl;

Y represents a linear or branched ($C_1$–$C_4$) alkyl, acyl, aryl, arylalkyl;

W and Z, equal or different, represent a linear or branched ($C_1$–$C_4$) alkyl, arylalkyl, methoxyethyl, methoxypropyl, methoxybenzyl;

or the $$-\overset{R_7}{\underset{|}{N}}-(CH_2)_n-X,$$

group is an heterocyclic group such as for example provided that when $R_3$ = $R_4$ = H, $R_1$ and $R_2$ cannot both be H, and when $R_7$ is H and n is O, X cannot be methyl.

The process for the preparation of the compounds of the invention is described for the compound having formula (II)

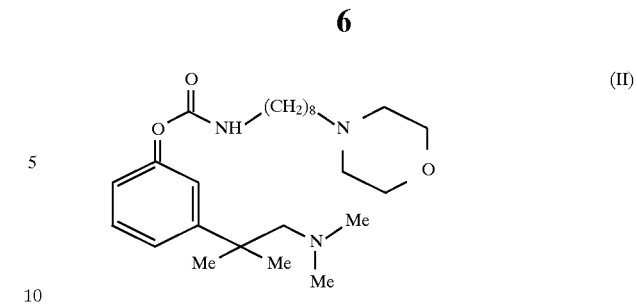

but, as it will be evident from the examples, the same process may be used for the preparation of all the compounds having formula (I) using suitable reacting substances. The compound having formula (II) is prepared through the following steps:

A) The compound having formula (III)

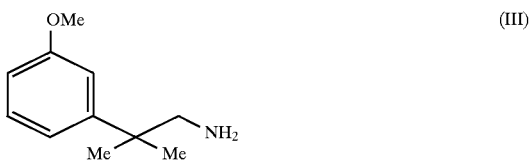

is made to react with formaldehyde and in reductive amination conditions to obtain the compound (IV)

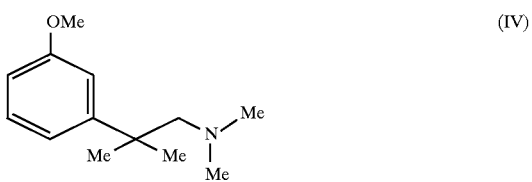

B) The compound having formula (IV) is o-demethylated in acidic conditions to obtain the compound having formula (V)

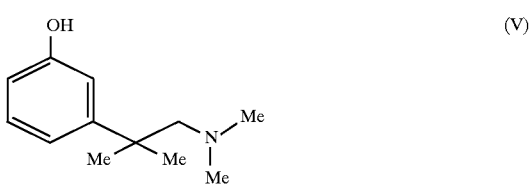

C) The compound having formula (VI)

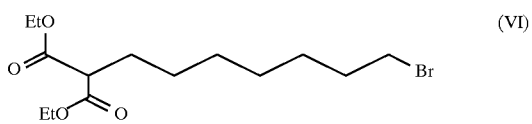

is made to react with morpholine to obtain the compound (VII)

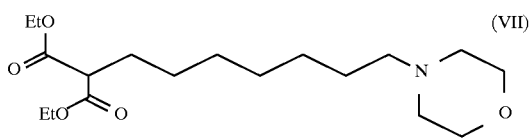

D) The compound (VII) is monodecarboxylated to obtain the compound (VIII)

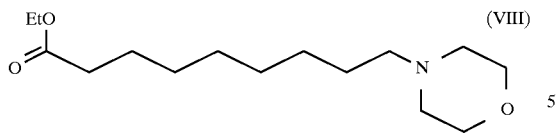

E) The compound (VIII) is submitted to hydrolysis, then transformed in acylazide and by Curtius rearrangement in isocyanate to obtain the compound (IX)

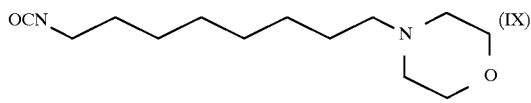

F) The compound (V) dissolved in anhydrous toluene, is treated with metallic sodium and subsequently with the compound (IX) to obtain the desired compound (II).

The A) step is carried out preparing a solution in a polar or bipolar aprotic solvent such as methanol, ethanol or acetonitrile of the compound (III) and of formaldehyde in 1:10 molar ratio and adding to this solution a reducing agent as sodium borohydride or sodium cyanoborohydride with 4:1 molar ratio between this compound and the compound (III), cooling the solution so that the temperature is maintained between 2° and 5° C.

The same reaction may be carried out in formic acid and formaldehyde at a temperature between 50° and 100° C.

The B) step is carried out treating the compound (IV) with an aqueous solution of HBr at 48% by weight at a temperature between 25° and 100° C., or using a Lewis acid such as aluminium trichloride, boron trifluoride, boron tribromide at a temperature between 25° C. and 80 ° C. in an apolar solvent such as benzene, toluene or chlorobenzene.

In the C) step compound (VI) is made to react with morpholine with molar ratio between (VI) and morpholine between 1:2 and 1:3 in an aprotic bipolar solvent such as for example dimethylformamide, dimethylsulfoxyde, acetone, acetonitrile at room temperature.

The D) step is carried out making the compound (VII) to react with boric acid with molar ratio between (VII) and boric acid between 1:1 and 1:2 at the acid melting point. The reaction may also be carried out in dimethyl sulfoxide in presence of sodium chloride at a temperature between 100° and 160° C. or heating to fusion the compound (VII) with stearic acid in presence of tetrabutyl phosphonium bromide.

The E) step is carried out treating the compound (VIII) with sodium hydroxide in water to boiling to obtain the sodic salt from it; acetone, tetrabutyl ammonium chloride and ethyl chloroformate dissolved in acetone at a temperature between −5° and 0° C. are added to it, after cooling, in order to form the mixed anhydride.

The latter by treatment with sodium azide dissolved in water at 0° C. provides the acylazide which heated to boiling is transformed into isocyanate. The used molar ratios have been the following ones: compound (VIII)/ethyl chloroformate between 1:1 and 1:2 and compound (VIII)/sodium azide between 1:2 and 1:3.

In the F) step the compound (V) dissolved in an apolar solvent such as benzene, xylene, chlorobenzene, toluene is treated with metallic sodium in a molar ratio between (V) and Na between 10:1 and 20:1 and subsequently with the compound (IX) at room temperature with a molar ratio between (V) and (IX) between 1:1 and 1:2.

As an alternative to the described process the compounds having general formula (I) may be prepared by treatment of chloromethylcarbonate having formula (X)

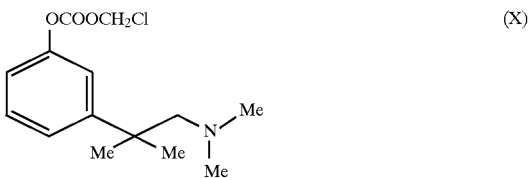

with the suitable amine at room temperature in a bipolar aprotic solvent such as acetonitrile, dimethyl sulfoxide and dimethylformamide with a molar ratio between (X) and amine between 1:1 and 1:2.

For the formulation in pharmaceutical compositions the compounds having general formula (I) may be salified with acids selected from the group comprising HCl, HBr, $H_2SO_4$, $H_3PO_4$, $HClO_4$, $CH_3SO_3H$, p-toluensulfonic acid, citric acid, tartaric acid, maleic acid, salicylic acid, fumaric acid, succinic acid, oxalic acid, and so on.

For explanatory aim of the process for the preparation of the compounds according to the invention the following examples are reported.

EXAMPLE 1

Synthesis of 3-[(1-dimethylamino-2-methyl)prop-2-yl]-N-[8-(4-morpholinyl) octyl]phenylcarbamate (II)

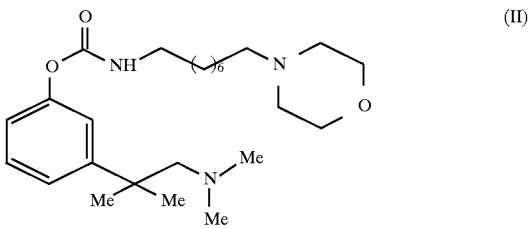

1A) N,N-2-trimethyl-2-(3-methoxyphenyl)propylamine (IV)

25.3 g (0.403 moles) of sodium cyanoborohydride are added portion by portion and cooling so that the temperature does not exceed 5° C. to a solution of 24.0 g (0.134 moles) of 2-methyl-2-(3-methoxyphenyl) propylamine (III) and 93 ml (1.34 moles) of formaldehyde (40% in water) in 250 ml of acetonitrile. After 15' it is taken to pH=7 with glacial acetic acid and left to room temperature for 1 h. The solvent is evaporated at reduced pressure, the residue is taken back with diethyl ether and an acid-base wash is performed. The organic phase is dehydrated and evaporated at reduced pressure obtaining a yellowish oil constituted by 23.71 g of N,N,2-trimethyl-2-(3-methoxyphenyl)propylamine.

Yield=85%

| Elemental analysis | C | H | N |
| --- | --- | --- | --- |
| (theor. %) | 73.51 | 10.21 | 6.76 |
| (found %) | 75.22 | 10.08 | 6.85 |

IR (film,cm $^{-1}$): 1040 (ν C—O—C)
$^1$H-NMR(CDCl$_3$,ppm): 7.22(1H,t); 6.96(2H,m); 6.71(1H, m); 3.79(3H,s); 2.45(2H,s); 2.07(6H,s); 1.31(6H,s).

1B) 3-[(1-dimethylamino-2-methyl)prop-2-yl]phenol (V)

A solution constituted by 10 g (48.2 mmoles) of N,N,2-trimethyl-2-(3-methoxyphenyl) propylamine (IV) in 180 ml of hydrobromic acid at 48% in water is heated to reflux for 4 h. At the end it is concentrated it reduced pressure, it is alkalized to pH=9 and extracted by diethyl ether. The organic phase evaporated at reduced pressure gives a yellowish oil which is crystallized by petroleum ether: isopropyl ether/10:1. 6.84 g of a whitish solid constituted by 3-[(1-dimethylamino-2-) methyl)prop-2-yl]phenol are obtained.

Yield=73%

| Elemental analysis | C | H | N |
|---|---|---|---|
| (theor. %) | 74.57 | 9.91 | 7.25 |
| (found %) | 74.33 | 9.72 | 7.12 |

$^1$H-NMR(CDCl$_3$,ppm): 7.19(1H,m); 6.90(1H,m); 6.75 (1H,m); 6.65(1H,m); 2.58(2H,s); 2.09(6H,s); 1.29(6H,s).

1C) 7-(4-morpholinyl)heptyl diethyl malonate (VII).

16 ml (183 mmoles) of morpholine are added to a solution of 28.1 g (83.3 mmoles) of 7-bromo heptyl diethyl malonate (VI) (obtained as described in Bull. Soc. Chim. Fr. 1463 (1957)) in 150 ml of anhydrous acetonitrile and it is left under agitation at room temperature for 20 h.

After such a period the precipitated solid (morpholine hydrobromide) is filtered and washed with little acetonitrile. The solvent is evaporated at reduced pressure and the residue taken back by ethyl acetate and washed with water. The separated organic phase is dehydrated and evaporated at reduced pressure obtaining 28.0 g of 7-(4- morpholinyl) heptyl diethyl malonate.

Yield=98%

| Elemental analysis | C | H | N |
|---|---|---|---|
| (theor. %) | 62.95 | 9.68 | 4.08 |
| (found %) | 62.49 | 9.57 | 4.13 |

IR (film,cm$^{-1}$): 1745, 1730 (ν C=O).

1D) 9-(4-morpholinyl) ethyl nonanoate (VIII) 27.0 g (78.4 mmoles) of 7-(4-morpholinyl) heptyl diethyl malonate (VII) and 7.3 g (118 mmoles) of boric acid are heated for 5–6 h at the boric acid melting point (170° C.), distilling the ethanol formed during the reaction.

The reaction mixture is then poured in water and extracted by ethyl acetate. The organic phase is dehydrated and evaporated at reduced pressure obtaining 16.6 g of 9-(4-morpholinyl) ethyl nonanate.

Yield=78%

| Elemental analysis | C | H | N |
|---|---|---|---|
| (theor. %) | 66.38 | 10.77 | 5.16 |
| (found %) | 65.91 | 10.81 | 5.23 |

IR (film,cm$^{-1}$): 1730 (ν C=O)

$^1$H-NMR(CDCl$_3$,ppm): 4.05(2H,q); 3.65(4H,t); 2.36(4H,t); 2.30–2.17(4H,m);1.63–1.23(12H,m); 1.19(3H,t);

1E) 8-(4-morpholinyl)octyl isocyanate (IX).

16.5 g (60.9 mmoles) of 9-(4-morpholinyl)ethyl nonanoate (VIII) are suspended in 50 ml of water, 2.68 g (67.0 mmoles) of sodium hydroxide are added and it is heated to reflux for 30'. At the end the reaction mixture is cooled and extracted by ethyl acetate. 25 ml of acetone, 0.82 g (2.95 mmoles) of tetrabutylammonium chloride are added to the aqueous phase containing the sodic salt and 6.4 ml (78.4 mmoles) of ethyl chloroformate, dissolved in 25 ml of acetone, are dropped, keeping the temperature between −5° C. and 0° C. After 1 h 8.71 g (134 mmoles) of sodium azide dissolved in 50 ml of water are dropped in the reaction mixture and it is left under agitation at 0° C. for 1 h. After such a period the mixture is extracted several times by toluene, the organic extracts are reunited, dehydrated and heated to 80° C. for 1 h.

At the end it is evaporated at reduced pressure and the residue is distilled at 140°–143° C. and 2.5 mmHg. 6.0 g of 8-(4-morpholinyl)octyl isocyanate are obtained.

Yield=41%

| Elemental analysis | C | H | N |
|---|---|---|---|
| (theor. %) | 64.96 | 10.06 | 11.65 |
| (found %) | 64.39 | 10.19 | 11.44 |

IR (film,cm$^{-1}$): 2270 (ν N=C=O)

$^1$H-NMR(CDCl$_3$,ppm): 3.7(4H,t); 3.25(2H,t); 2.40(4H,t); 2.30(2H,q); 1.70–1.20(12H,m).

1F) 3-[(1-dimethylamino-2-methyl)prop-2-yl]-N-[8-(4-morpholinyl)octyl]-phenylcarbamate (II)

10 mg of metallic sodium are added to a solution of 3.0 g (15.5 moles) of 3-[(dimethylamino-2-methyl)prop-2-yl] phenol (V) in 120 ml of anhydrous toluene at room temperature and in inert atmosphere; after 5' a solution of 4.1 g (17.1 moles) of 8-(4-morpholinyl)octyl isocyanate (IX) in 70 ml of anhydrous toluene is slowly dropped. After 1.5 h the sodium in excess is removed and it is evaporated at reduced pressure.

6.51 g of 3-[(1-dimethylamino)2-methyl)prop-2-yl]-N-8-(4-morpholinyl) octyl]-phenylcarbamate (II) yellowish oil-shaped are obtained.

Yield=97%

| Elemental analysis | C | H | N |
|---|---|---|---|
| (theor. %) | 69.25 | 10.00 | 9.69 |
| (found %) | 68.88 | 10.08 | 9.75 |

IR (film,cm $^{-1}$) 3350 (ν N—H); 1740, 1720 (ν C=O)

$^1$H-NMR(CDCl$_3$,ppm):7.32–7.15(2H,m);7.12(1H,t);6.94 (1H,dt) 5.03(1H,t); 3.72(4H,t); 3.25(2H,q); 2.44(6H,m); 2.31(2H,m); 2.07(6H,m); 1.31(18H,s).

EXAMPLE 2

Synthesis of 3-[(1-dimethylamino-2-methyl)-prop-2-yl]-N-8-[[4-(cis2,6-dimethyl) morpholinyl]octyl]-phenylcarbamate.

Preparation of 7-[4-(cis 2,6-dimethyl)morpholinyl] heptyl diethyl malonate

Acting as described in the Example 1 point 1C) but using as amine the cis 2,6-dimethylmorpholine one obtains the 7-[4-(cis 2,6-dimethyl)morpholinyl]heptyl diethyl malonate.

Yield=84%

| Elemental analysis | C | H | N |
|---|---|---|---|
| (theor. %) | 64.66 | 10.04 | 3.77 |
| (found %) | 64.22 | 10.21 | 3.85 |

IR (film,cm$^{-1}$): 1750, 1730 (ν C=O)

Preparation of 9-[4-(cis 2,6-dimethyl)morpholinyl] ethyl nonanoate

Using 7-[4-(cis 2,6-dimethyl)morpholinyl]heptyl diethyl malonate and acting as described in the Example 1 point 1D) one obtains 9-[4-(cis 2,6-dimethyl) morpholinyl]ethyl nonanoate.

Yield=81%

| Elemental analysis | C | H | N |
|---|---|---|---|
| (theor. %) | 68.18 | 11.11 | 4.68 |
| (found %) | 67.97 | 11.31 | 4.74 |

IR (film,cm$^{-1}$): 1730 (ν C=O).

Preparation of 8-[4-(cis 2,6-dimethyl)morpholinyl] octyl isocyanate

Using 9-[4-(cis 2,6-dimethyl)morpholinyl]ethyl nonanoate and acting as described in the example 1 point 1E) one obtains 8-[4-(cis 2,6-dimethyl morpholinyl]octyl isocyanate.

Yield=50%

| Elemental analysis | C | H | N |
|---|---|---|---|
| (theor. %) | 67.12 | 10.50 | 10.44 |
| (found %) | 67.61 | 10.69 | 10.55 |

IR (film,cm$^{-1}$): 2260 (ν N=C=O)

1H-NMR(CDCl$_3$ppm): 3.35(2H,m); 3.15(2H,t); 2.38(2H, dt); 2.25(2H,dd); 1.70(2H,dd);1.60–1.20(12H,m); 1.10(6H, d).

Preparation of 3-[(1-dimethylamino-2-methyl)-prop-2-yl]-N-8[4-(cis 2,6-dimethyl) morpholinyl]octyl-phenyl carbamate 3.80 g of 3-[(1-dimethylamino-2-methyl)prop-2-yl]-N-[8-[4-(cis 2,6-dimethyl)morpholinyl]octyl]-phenylcarbamate are obtained from 2.09 g (10.8 mmoles) of 3-[(1-dimethylamino-2-methyl)-prop-2-yl]phenol and 2.90 g (10.8 mmoles) of 8-[4-(cis 2,6-dimethyl)morpholinyl] octyl isocyanate using the method described in the Example 1 point 1F).

Yield=76%

| Elemental analysis | C | H | N |
|---|---|---|---|
| (theor. %) | 70.24 | 10.26 | 9.10 |
| (found %) | 70.57 | 10.03 | 8.98 |

IR (film,cm$^{-1}$): 3320 (ν N—H); 1740, 1715 (ν C=O)

$^1$H-NMR(CDCl$_3$,ppm): 7.27(1H,t); 7.20(1H,dt); 7.11(1H, d); 6.94(1H,dt); 5.00(1H,t); 3.68(2H,m); 3.25(2H,q); 2.74 (2H,dt); 2.43(2H,s); 2.28(2H,dd); 2.10(6H,s); 1.70(2H,dd); 1.60–1.40(12H,m); 1.35(6H,s); 1.15(6H,d).

EXAMPLE 3

Synthesis of 3-[(1-dimethylamino-2-methyl)prop-2-yl]-N-[8-[4-(trans 2,6-dimethyl morpholinyl]octyl]-phenylcarbamate

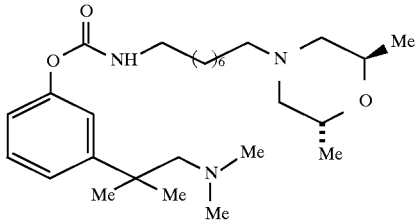

Preparation of 8-[4-(trans 2,6-dimethyl) morpholinyl]octyl isocyanate

Acting as described in the Example 1 points 1C), 1D), 1E) but using trans 2,6-dimethylmorpholine (obtained as described in the Pat. DE 2,656,747) one obtains 8-[4-(trans 2,6-dimethyl)morpholinyl]octyl isocyanate.

| Elemental analysis | C | H | N |
|---|---|---|---|
| (theor. %) | 67.12 | 10.50 | 10.44 |
| (found %) | 66.85 | 10.39 | 10.27 |

Preparation of 3-[(1-dimethylamino-2-methyl)-prop-2-yl]-N-[8-[4-(trans 2,6-dimethyl)morpholinyl] octyl]-phenylcarbamate 1.67 g of 3-[(1-dimethylamino-2-methyl)prop-2-yl]-N-[8-[4-(trans 2,6-dimethyl morpholinyl]octyl]-phenylcarbamate are obtained from 1.0 g (5.17 mmoles) of 3-[(1-dimethylamino-2-methyl)prop-2-yl]phenol and 1.4 g (5.17 mmoles) of 8-[4-(trans 2,6-dimethyl) morpholinyl] octyl isocyanate using the method described in the Example 1 point 1F).

Yield=70%

| Elemental analysis | C | H | N |
|---|---|---|---|
| (theor. %) | 70.24 | 10.26 | 9.10 |
| (found %) | 70.63 | 10.11 | 9.32 |

IR (film,cm$^{-1}$): 3320 (ν N—H); 1740, 1715 (ν C=O)

$^1$H-NMR(CDCl$_3$ppm): 7.28(1H,t); 7.19(1H,dt); 7.10(1H, d); 6.90(1H,dt); 5.35(1H,t); 3.60(2H,m); 3.15(2H,q); 2.70 (2H,m); 2.40(2H,s); 2.20(2H,m); 2.00(6H,s); 1.60(2H,t); 1.20(18H,m); 1.05(6H,d).

EXAMPLE 4

Synthesis of 3-[(1-dimethylamino-2-methyl)prop-2-yl]-N-butylphenyl carbamate

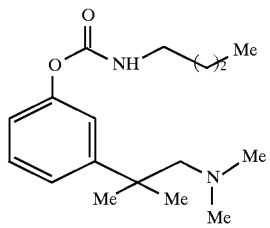

0.48 g of 3-[(1-dimethylamino-2-methyl)prop-2-yl]-N-butylphenyl carbamate are obtained from 0.4 g (2.0 mmoles) of 3-[(1-dimethylamino-2-methyl)prop-2-yl]phenol and 0.2 g (2.0 mmoles) of butyl isocyanate using the method described in the Example 1 point 1F).

Yield=80%

| Elemental analysis | C | H | N |
|---|---|---|---|
| (theor. %) | 69.82 | 9.65 | 9.58 |
| (found %) | 69.50 | 9.75 | 9.30 |

IR (film,cm$^{-1}$): 3330 (ν N—H); 1740, 1720 (ν C=O)
$^1$H-NMR(CDCl$_3$,ppm): 7.35–6.80(4H,m); 4.92(1H,s all); 3.21(2H,q); 2.40(2H,s); 2.02(6H,s); 1.42(4H,m); 1.27(6H,s); 0.87(3H,t).

EXAMPLE 5

Synthesis of 3-[(1-dimethylamino-2-methyl)prop-2-yl]-N-heptyl-phenyl carbamate

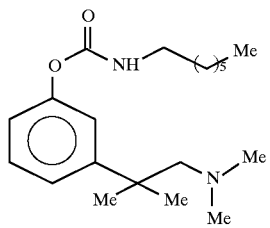

0.21 g of 3-[(1-dimethylamino-2-methyl)prop-2-yl]-N-heptyl-phenyl carbamate are obtained from 0.16 g (0.83 mmoles) of 3-[(1-dimethylamino-2-methyl)prop-2yl]phenol and 0.12 g (0.83 mmoles) of heptyl isocyanate using the method described in the Example 1 point 1F).

Yield=75%

| Elemental analysis | C | H | N |
|---|---|---|---|
| (theor. %) | 71.81 | 10.24 | 8.37 |
| (found %) | 71.49 | 9.95 | 8.00 |

IR (film,cm$^{-1}$): 3320 (ν N—H); 1740, 1720 (ν C=O)
$^1$H-NMR(CDCl$_3$,ppm): 7.35–6.80(4H,m); 4.92(1H,s all); 3.21(2H,q); 2.40(2H,s); 2.07(6H,s); 1.60–1.10(10H,m); 1.27(6H.s); 0.80(3H,t).

EXAMPLE 6

Synthesis of 3-[(1-dimethylamino-2-methyl)prop-2-yl]-N-[4-(4-morpholinyl)butyl]-phenyl carbamate.

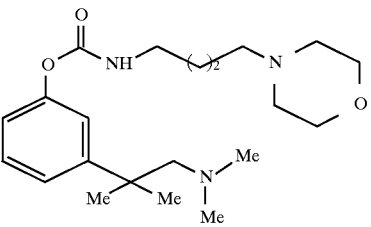

Preparation of 4-(4-morpholinyl)butyl isocyanate

A solution constituted by 3.16 g (0.02 moles) of 4-(4-morpholinyl)butyl amine and 16.7 ml (0.12 moles) of triethylamine in 60 ml of toluene is dropped in 15.5 ml (0.03 moles) of phosgene (20% in toluene) kept at 0° C. and in inert atmosphere for about 20'. It is left to react at 0° C. for 3 h and then the solvent is removed at reduced pressure. The residue taken beck by dioxane gives a white solid (triethyl amine hydrocloride) which is filtered. The dioxane is evaporated at reduced pressure and the obtained residue distilled between 200° and 240° C. at 0.5 mmHg. 2.4 g of 4-(4-morpholinyl)butyl isocyanate are recovered.

Yield=65%

| Elemental analysis | C | H | N |
|---|---|---|---|
| (theor. %) | 58.67 | 8.75 | 15.21 |
| (found %) | 58.42 | 8.50 | 14.98 |

IR (film,cm$^{-1}$): 2280 (ν N=C=O).

Preparation of 3-[(1-dimethylamino-2-methyl)prop-2-yl]-N-[4-(4-morpholinyl)butyl]-phenyl carbamate 0.73 g of 3-[(1-dimethylamino-2-methyl)prop-2-yl]-N-[4-(4-morpholinyl)butyl]-phenyl carbamate are obtained from 0.45 g (1.67 mmoles) of the 3-[(1-dimethylamino-2-methyl)prop-2-yl]phenol and 0.43 g (1.67 mmoles) of 4-(4-morpholinyl)butyl isocyanate using the method described in the Example 1 point 1F).

Yield=83%

| Elemental analysis | C | H | N |
|---|---|---|---|
| (theor. %) | 66.81 | 9.34 | 11.13 |
| (found %) | 66.55 | 9.37 | 10.85 |

IR (film,cm$^{-1}$): 3340 (ν N—H); 1735, 1725 (ν C=O)
$^1$H-NMR(CDCl$_3$,ppm): 7.36–6.85(4H,m); 5.04(1H,s all); 3.71(4H,m); 3.25(2H,q); 2.49–2.20(8H,m); 2.15(6H,s); 1.60 (4H,m); 1.35(6H,s).

EXAMPLE 7

Synthesis of 3-[2-(dimethylamino)ethyl]-N-[8-(morpholinyl)octyl]-phenyl carbamate

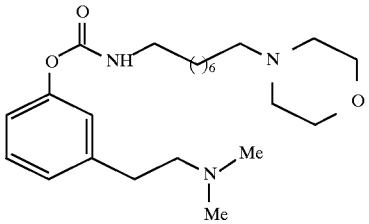

1 g of 3-[2-(dimethylamino)ethyl]-N-[8-(4-morpholinyl) octyl]-phenyl carbamate is obtained from 0.50 g (3.03 mmoles) of 3-[2-(dimethylamino)ethyl]phenol and 0.73 g (3.03 mmoles) of 8-(4-morpholinyl)octyl isocyanate using the method described in the Example 1 point 1F).
Yield=80%

| Elemental analysis | C | H | N |
|---|---|---|---|
| (theor. %) | 68.11 | 9.69 | 10.36 |
| (found %) | 67.94 | 9.84 | 10.08 |

IR (film,cm$^{-1}$): 3360 (ν N—H); 1740, 1720 (ν C═O)
$^1$H-NMR(CDCl$_3$,ppm): 7.30(1H,t); 7.00(3H,m); 5.20(1H, t); 3.70(4H,t); 3.25(2H,q); 2.80–2.50(4H,m); 2.45(4H,t); 2.35(2H,m); 2.30(6H,s); 1.30(12H,m).

EXAMPLE 8

Synthesis of the 3-[(1-dimethylamino)prop-2-yl]-N-[-(4-morpholinyl)octyl]-phenyl carbamate

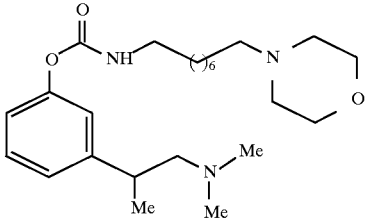

Preparation of 3-[(1-dimethylamino)prop-2-yl] phenol

Using N,N-dimethyl-2-(3-methoxyphenyl)propylamine and acting as described in the Example 1 point 1B) 3-[(1-dimethylamino)prop-2-yl]phenol is obtained.
Yield=77%

| Elemental analysis | C | H | N |
|---|---|---|---|
| (theor. %) | 73.70 | 9.56 | 7.81 |
| (found %) | 73.37 | 9.62 | 7.74 |

IR (film,cm$^{-1}$): 3300 (ν O—H)
$^1$H-NMR(CDCl$_3$,ppm): 7.58(1H,m); 7.00(1H,t); 6.60(1H, m); 6.40(2H,m); 3.28(2H,m); 2.35(1H,q); 2.20(6H,s); 1.10 (3H,d).

Preparation of 3-[(1-dimethylamino)prop-2-yl]-N-[8-(4-morpholinyl)octyl]-phenyl carbamate 0.79 g of 3-[(1-dimethylamino)prop-2-yl]-N-[8-(4-morpholinyl)octyl]-phenyl carbamate are obtained from 0.45 g (2.5 mmoles) of 3-[(1-dimethylamino)prop-2-yl] phenol and 0.62 g (2.5 mmoles) of 8-(4-morpholinyl)octyl isocyanate using the method described in the Example 1 point 1F).
Yield=75%

| Elemental analysis | C | H | N |
|---|---|---|---|
| (theor. %) | 68.70 | 9.85 | 10.01 |
| (found %) | 68.28 | 9.96 | 10.11 |

IR (film,cm$^{-1}$): 3350 (ν N—H); 1730, 1710 (ν C═O)
$^1$H-NMR(CDCl$_3$,ppm): 7.10 (1H,t); 6.95(3H,m); 5.25 (1H,t); 3.60(4H,t); 3.18(2H,q); 2.80(1H,q); 2.38(4H,t); 2.25 (4H,m); 2.18(6H,s); 1.40–1.30(12H,m); 1.20(3H,d).

EXAMPLE 9

Synthesis of 3-[2-(dimethylamino)propyl]-N-[8-(4-morpholinyl)octyl]-phenyl carbamate

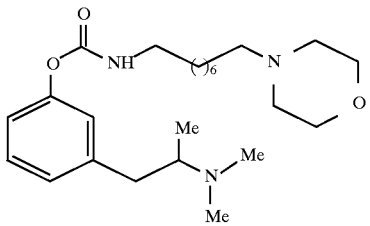

Preparation of 3-[2-(dimethylamino)propyl]phenol

Using N,N,2-trimethyl-(3-methoxyphenyl)ethylamine and acting as described in the Example 1 point 1B) 3-[2-(dimethylamino)propyl]phenol is obtained.
Yield=76%

| Elemental analysis | C | H | N |
|---|---|---|---|
| (theor. %) | 73.70 | 9.56 | 7.81 |
| (found %) | 73.81 | 9.45 | 7.70 |

IR (film,cm$^{-1}$): 3450 (ν O—H)
$^1$H-NMR(CDCl$_3$,ppm): 7.40 (1H,m); 7.10(1H,t); 6.90 (3H,m); 2.80(2H,m); 2.30(1H,q); 2.20(6H,s); 0.80(3H,d).

Preparation of 3-[2-(dimethylamino)propyl]-N-[8-(4-morpholinyl)octyl]-phenyl carbamate 1.02 g of 3-[2-(dimethylamino)propyl]-N-[8-(4-morpholinyl)octyl]-phenyl carbamate are obtained from 0.51 g (2.8 mmoles) of 3-[2-(dimethylamino)propyl]phenol and 0.68 g (2.8 mmoles) of 8-mopholinyl) octyl isocyanate using the method described in the Example 1 point 1F).
Yield=86%

| Elemental analysis | C | H | N |
|---|---|---|---|
| (theor. %) | 68.70 | 9.85 | 10.01 |
| (found %) | 68.38 | 9.93 | 10.18 |

IR (film,cm$^{-1}$): 3320 (ν N—H); 1740 (ν C═O)
$^1$H-NMR(CDCl$_3$,ppm): 7.10 (1H,t); 6.90(3H,m); 5.20 (1H,t); 3.65(4H,t); 3.18(2H,q); 2.90(2H,dd); 2.70(1H,m); 2.37(4H,t); 2.28(2H,m); 2.25(6H,s); 1.50–1.30(12H,m); 0.80(3H,d).

EXAMPLE 10

Synthesis of 4-[2-(dimethylamino)propyl]-N-butyl-phenyl carbamate

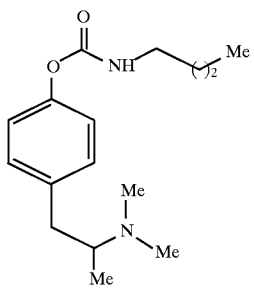

0.6 g of 4-[2-(dimethylamino)propyl]-N-butyl-phenyl carbamate are obtained from 0.50 g (2.79 mmoles) of 4-[2-(dimethylamino)propyl]phenol and 0.28 g (2.79 mmoles) of the butyl isocyanate using the method described in the Example 1 point 1F).

Yield=77%

| Elemental analysis | C | H | N |
|---|---|---|---|
| (theor. %) | 69.03 | 9.41 | 10.06 |
| (found %) | 68.77 | 9.50 | 10.20 |

IR (film,cm$^{-1}$): 3320 (ν N—H); 1730 (ν C=O)

$^1$H-NMR(CDCl$_3$,ppm): 7.12–6.88(4H,m); 4.93(1H,t); 3.22(2H,q); 3.00–2.60(3H,m); 2.25(6H,s);1.66–1.20(4H, m); 0.95–0.80(6H,m).

EXAMPLE 11

Synthesis of 4-[2-(dimethylamino)propyl]-N-heptyl-phenyl carbamate

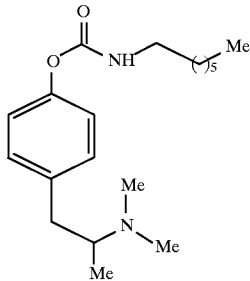

0.38 g of 4-[2-(dimethylamino)propyl]-N-heptyl-phenyl carbamate are obtained from 0.30 g (1.67 mmoles) of 4-[2-(dimethylamino)propyl]phenol and 0.24 g (1.67 mmoles) of heptyl isocyanate using the method described in the Example 1 point 1F).

Yield=71%

| Elemental analysis | C | H | N |
|---|---|---|---|
| (theor. %) | 71.43 | 9.78 | 8.77 |
| (found %) | 71.09 | 9.55 | 8.67 |

IR (film,cm$^{-1}$): 3320 (ν N—H); 1730 (ν C=O)

$^1$H-NMR(CDCl$_3$,ppm): 7.15–6.90(4H,m); 4.95(1H,t); 3.20(2H,q); 2.85–260(3H,m); 2.32(6H,s); 1.50–1.15(10H, m); 0.95–0.82(6H,m).

EXAMPLE

Synthesis of 3-[(1-dimethylamino-2-methyl)prop-2-yl]-N-[4-(4-amino-6,7-dimethoxy)quinazolin -2-yl] piperazinyl]-8-octanoyl]-phenyl carbamate

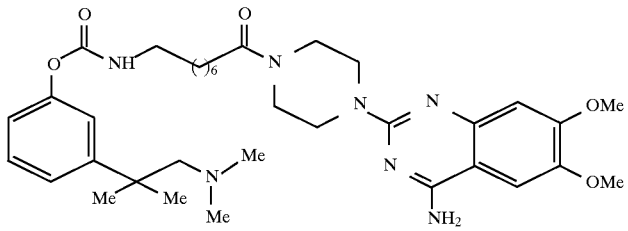

12A) 4-[(4-amino-6,7-dimethoxy)quinazolin-2-yl]-1-(8-bromooctanoyl) piperazine 2.1 ml (0.015 moles) of anhydrous triethylamine and subsequently 1.4 ml (0.015 moles) of ethylchloroformate are added at 0° C. and under inert atmosphere to a solution constituted by 5.0 g (0.022 moles) of 8-bromooctanoic acid in 50 ml of anhydrous dimethylformamide. It is taken to room temperature and after 1.5 h 3.6 g (0.012 moles) of 1-[(4-amino-6,7-dimethoxy) quinazolin-2-yl]piperazine (obtained as described in J. Med. Chem. 20, 146 (1977)) dissolved in 80 ml of anhydrous dimethylformamide are added.

After 4 h the solvent is evaporated at reduced pressure and the obtained residue is washed in water and filtered.

5.50 g of 4-[(4-amino-6,7-dimethoxy)quinazolin-2-yl]-1-(8-bromooctanoyl)piperazine are isolated.

Yield=93%

| Elemental analysis | C | H | N |
|---|---|---|---|
| (theor. %) | 53.44 | 6.52 | 14.16 |
| (found %) | 52.88 | 6.74 | 13.84 |

IR (nujol,cm$^{-1}$): 3380, 3340, 3220 (ν N—H); 1650 (ν C=O)

¹H-NMR(CDCl₃,ppm): 7.05(1H,s); 6.90(1H,s); 5.50 (2H,s broad); 3.92(3H,s); 3.90(3H,s); 3.85(2H,m); 3.78(2H, m); 3.65(2H,m); 3.50(2H,m); 3.35(2): 2.32(2H,t); 1.80(2H, m); 1.58(2H,m); 1.30(6H,m).

12B) 4-[(4-amino-6,7-dimethoxy)quinazolin-2-yl]-1-(8-phthalimido octanoyl)piperazine 26.73 g (0.054 moles) of 4-[(4-amino-6,7-dimethoxy) quinazolin-2-yl]-1-(8-bromooctanoyl) piperazine, 10.01 g (0.054 moles) of potassium phthalimide and 0.1 g of sodium iodide (catalytic quantity) are suspended in 500 ml of anhydrous dimethylformamide and heated to 80° C. for 15 h. At the end the solvent is evaporated at reduced pressure, 300 ml of water are added and it is extracted by chloroform. The organic phase is dehydrated, evaporated at reduced pressure and chromatographed on silica gel using petroleum ether: chloroform: methanol: triethylamine/8:5:1:1 as eluant.

The end fractions are gathered and dried.

23.12 g of 4-[(4-amino-6.7-dimethoxy)quinazolin-2-yl]-1-(8-phthalimido octanoyl)piperazine as a yellowish solid are obtained.

Yield=76% m.p.=172.5°–174° C.

| Elemental analysis | C | H | N |
|---|---|---|---|
| (theor. %) | 64.27 | 6.47 | 14.99 |
| (found %) | 63.88 | 6.74 | 15.32 |

IR (nujol,cm⁻¹): 3430, 3330, 3200 (v N—H); 1760, 1700, 1620 (v C=O)

¹H-NMR(CDCl₃,ppm): 7.78(2H,m); 7.65(2H,m); 6.85 (1H,s); 6.75(1,s); 5.16(2H,s); 3.92(3H,s); 3.86(3H,s); 3.76 (4H,m); 3.61(4H,m); 3.45(2H,m); 2.30(2H,m); 1.60(4H,m); 1.30(6H,m).

12C) 4-[(4-amino-6,7-dimethoxy)quinazolin-2-yl]-1-(8-aminooctanoyl) piperazine

An etherogeneous solution constituted by 1.92 g (3.42 mmoles) of 4-[(4-amino-6,7-dimethoxy)quinazolin-2-yl]-1-(8-phthalimido octanoyl)piperazine and 0.5 ml (8.2 mmoles) of hydrazine monohydrate (80% in water) in 40 ml of ethanol is heated to reflux for 3 h. Then the solution is concentrated to about half the volume and added with 2 ml of hydrochloric acid at 36%. The obtained precipitate is filtered and washed with ethanol; the bitterns are evaporated at reduced pressure and the residue is taken back with 10 ml of water. It is taken to pH=10 by sodium hydroxide and extracted by chloroform.

The separated organic phase is dehydrated and evaporated obtaining 1.40 g of a whitish solid constituted by 4-[(4-amino-6,7-dimethoxy) quinazolin-2-yl]-1-(8-aminooctanoyl) piperazine.

Yield=96%

| Elemental analysis | C | H | N |
|---|---|---|---|
| (theor. %) | 61.37 | 7.96 | 19.52 |
| (found %) | 60.88 | 8.47 | 18.94 |

IR (nujol,cm⁻¹): 3400, 3340, 3220 (v N—H);

¹H-NMR(CDCl₃,ppm): 6.85(1H,s); 6.75(1,s); 5.20(2H,s); 3.91(3H,s); 3.85(3H,s); 3.75(4H,m); 3.65(2H,m); 3.45(2H, m); 2.60(2H,t); 2.30(2H,t); 1.58(2H,m); 1.45–1.25(10H,m).

12D) 3-[(1-dimethylamino-2-methyl)prop-2-yl]phenyl chloromethyl carbonate.

A solution of 0.10 ml (1.13 mmoles) of chloromethyl chloroformate in 10 ml of anhydrous methylene chloride is dropped at a temperature lower than 5° C. to a solution of 0.20 g (1.03 mmoles) of 3-[(l-dimethylamino-2-methyl) prop-2-yl]phenol and 0.15 ml (1.08 mmoles) of anhydrous triethylamine in 10 ml of anhydrous methylene chloride and it is left reacting for 2 h at room temperature. At the end it is washed first with a solution of sodium bicarbonate at 10% then with water.

The organic phase is dehydrated and evaporated at reduced pressure obtaining 0.28 g of 3-[(1-dimethylamino-2-methyl)prop-2-yl]phenyl chloromethyl carbonate.

Yield=95%

| Elemental analysis | C | H | N |
|---|---|---|---|
| (theor. %) | 58.84 | 7.05 | 4.90 |
| (found %) | 58.55 | 7.25 | 4.76 |

IR (film,cm⁻¹): 1770 (v C=O)

¹H-NMR(CDCl₃ppm): 7.30–7.00(4H,s); 5.75(2H,s); 2.47 (2H,s); 2.06(6H,m); 1.29(6H,s).

12E) 3-[(1-dimethylamino-2-methyl)prop-2-yl]-N-[1[-4-[ (amino-6.7 dimethoxy)quinazolin-2-yl]piperazinyl]-8-octanoyl]-phenyl carbamate.

0.45 g (1.05 mmoles) of 4-[(4-amino-6,7 dimethoxy) quinazolin-2-yl]-1-(8-aminooctanoyl) piperazine are added at room temperature to a solution of 0.30 g (1.05 mmoles) of 3-[(1-dimethylamino-2-methyl)prop-2-yl]phenyl chloromethyl carbonate in 7 ml of anhydrous dimethylformamide and it is left reacting for 1 h at room temperature. At the end 30 ml of water are added and it is extracted by chloroform. The dehydrated organic phase is evaporated at reduced pressure and the residue is chromatographed using petroleum ether: acetone: triethylamine/12:9:1 as eluant. 0.60 g of 3-[(1-dimethylamino-2-methyl)prop-2-yl]-N-[1-[4-(4-amino-6,7-dimethoxy) quinazolin-2-yl]piperazinyl]-8-octanoyl]-phenyl carbamate are obtained.

Yield=88%

| Elemental analysis | C | H | N |
|---|---|---|---|
| (theor. %) | 64.69 | 7.91 | 15.09 |
| (found %) | 64.33 | 7.75 | 15.15 |

¹H-NMR(CDCl₃,ppm): 7.21–6.80(6H,m); 5.17(2H,s widened); 5.00(1H,t); 3.99(3H,s); 3.91(3H,s); 3.85(4H,m); 3.70(2H,m); 3.52(2H,m); 3.25(2H,m); 2.48(2H,s); 2.38(2H, t); 2.10(6H,s); 1.70–1.10(16H,m).

EXAMPLE 13

Synthesis of 3-[(1-dimethylamino-2-methyl)prop-2-yl]-N-[N-[(4-amino-6,7-dimethoxy) quinazolin-2-yl] aminoheptyl]-phenyl carbamate

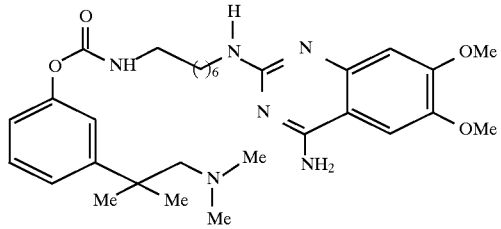

Preparation of N-[(4-amino-6,7-dimethoxy)quinazolin-2-yl] heptandiamine.

7.7 g (32 mmoles) of 4-amino-2-chloro-6,7-dimethoxyquinazoline are suspended in 250 ml of anhydrous butanol.

12.6 g (97 mmoles) of 1.7-diaminoheptane are added and the mixture is heated to reflux for 15 h. The solvent is evaporated at reduced pressure and the obtained residue is taken back by chloroform and washed by basic water.

12 g of raw product are obtained which by chromatographic purification (methylene chloride : methanol : ammonium hydroxyde 32% / 8:2:0.2 as eluant) gives 5.7 g of N-[(4-amino-6,7-dimethoxy)quinazolin-2-yl]heptandimine.
Yield=51%

| Elemental analysis | C | H | N |
|---|---|---|---|
| (theor. %) | 61.23 | 8.16 | 21.00 |
| (found %) | 61.15 | 8.24 | 20.87 |

IR (nujol,cm$^{-1}$): 3300, 3110 (v N—H)
$^1$H-NMR(CDCl$_3$,ppm): 7.40(1H,s); 6.95(2H,m); 6.65 (1H,s); 6.00(1H,m); 3.80(3H,s); 3.75(3H,s); 3.25(2H,m); 2.47(2H,m); 1.40-1.10(1OH,m).

Preparation of 3-[(1-dimethylamino-2-methyl)prop-2-yl]-N-[N-[(4-amino-6,7-dimethoxy) quinazolin-2-yl]aminoheptyl-phenyl carbamate 0.54 g of 3-[(1-dimethylamino-2-methyl)prop-2-yl]-N-[N-[4-amino-6,7-dimethoxy)quinazolin-2-yl]aminoheptyl-phenyl carbamate are obtained from 0.6 g (2.1 mmoles) of 3-[(1-dimethylamino-2-methyl)prop-2-yl]phenyl chloromethyl carbonate and 0.5 g of N-[(4-amino-6,7-dimethoxy) quinazolin-2-yl]heptandiamine using the method described in the Example 12 point 12E).
Yield=65%

| Elemental analysis | C | H | N |
|---|---|---|---|
| (theor. %) | 65.19 | 8.02 | 15.21 |
| (found %) | 65.07 | 8.11 | 15.09 |

IR (nujol,cm $^{-1}$): 3280 (v NHC=O); 3180 (v N—H); 1720 (v C=O)
$^1$H-NMR(CDCl$_3$,ppm): 7.70-(1,s); 7.50(2H,m); 7.30–7.10(4H,m); 6.95(1,m); 6.78(1H,s); 5.50(1H,t); 4.00 (3H,s); 3.90(3H,s); 3.40(2H,t); 3.30(2H,t); 2.60(2H,s); 2.15 (6H,s); 1.50–1.30(16H,m).

EXAMPLES FROM 14 TO 28

The following compounds have been prepared by processes analogous to those ones previously described:
3-[(1-dimethylamino-2-ethyl)-but-2-yl]-N-[8-(4-morpholinyl)octyl)]-phenylcarbamate (Example 14);
3-[(1-dimethylamino-2-methyl)-prop-2-yl]-N-[2-(4-morpholinyl)ethyl]-phenylcarbamate (Example 15);
3-[(1-(N-benzyl-N-methyl)amino-2-methyl)prop-2-yl]-N-[8-(4-morpholinyl)-octyl]-phenylcarbamate (Example 16);
3-[(1-dipropylamino-2-methyl)prop-2-yl]-N-[8-(4-morpholinyl)octyl]-phenylcarbamate (Example 17);
3-[(1-dimethylamino-2-methyl)prop-2-yl]-N-[10-(4-morpholinyl)decyl]-phenylcarbamate (Example 18);
3-[1(1-dimethylamino-2-methyl)prop-2-yl]-N-phenyl phenylcarbamate (Example 19);
3-[(1-dimethylamino-2-methyl)prop-2-yl]-N-(3-fluoro) phenyl phenylcarbamate (Example 20);
3-[(1-dimethylamino-2-methyl)prop-2-yl]-N-(3-methyl) phenyl phenylcarbamate (Example 21);
3-[(1-dimethylamino-2-methyl)prop-2-yl]-N-(3-methoxy) phenyl phenylcarbamate (Example 22);
3-[(1-dimethylamino-2-methyl)prop-2-yl]-N-(3-chloro) phenyl phenylcarbamate (Example 23);
3-[(1-dimethylamino-2-methyl)prop-2-yl]-N-benzyl-phenylcarbamate (Example 24);
3-[(1-dimethylamino-2-methyl)prop-2-yl]-N-phenyl-N-methyl-phenylcarbamate (Example 25);
3-[(1-dimethylamino-2-methyl)prop-2-yl]-N-(3-chloro)-phenyl-N-methyl-phenylcarbamate (Example 26);
3-[(1-dimethylamino-2-methyl)prop-2-yl]-N-ethyl-N-methyl-phenylcarbamate (Example 27);
3-[(1-dimethylamino-2-methyl)prop-2-yl]-N-indolinyl-phenylcarbamate (Example 28);
3-[(1-dimethylamino-2-methyl)prop-2-yl]-N-ethyl-N-phenyl phenylcarbamate (Example 29);
3-[(11-dimethylamino-2-methyl)prop-2-yl]-N-phenyl-N-propyl phenylcarbamate (Example 30);
3-[(1-dimethylamino-2-methyl)prop-2-yl]-N-(2-methoxy) phenyl-N-methyl phenylcarbamate (Example 31);
3-[(1-dimethylamino-2-methyl)prop-2-yl]-N-butyl-N-phenyl phenylcarbamate (Example 32),
3-[(1-dimethylamino-2-methyl)prop-2-yl]-N-methyl-N-(2-methyl)phenyl phenylcarbamate (Example 33);
3-[(1-dimethylamino-2-methyl)prop-2-yl]-N-cyclohexyl-N-ethyl phenylcarbamate (Example 34);
3-[(1-dimethylamino-2-methyl)prop-2-yl]-N-methyl-N-(4-methoxy)phenyl phenylcarbamate (Example 35);
3-[(1-dimethylamino-2-methyl)prop-2-yl]-N-ethyl-N-(4-methoxy)phenyl phenylcarbamate (Example 36);
3-[(1-dimethylamino-2-methyl)prop-2-yl]-N-(4-chloro) phenyl-N-methyl phenylcarbamate (Example 37);
3-[(1-dimethylamino-2-methyl)prop-2-yl]-N-(3-fluoro) phenyl-N-methyl phenylcarbamate (Example 38);
3-[(1-dimethylamino-2-methyl)prop-2-yl]-N-methyl-N-(3-trifluoromethyl) phenyl phenylcarbamate (Example 39);
3-[(1-dimethylamino-2-methyl)prop-2-yl]-N-cyclohexyl-N-methyl phenylcarbamate (Example 40).

PHARMACOLOGICAL EXPERIMENTATION

The compounds prepared as described in the above mentioned examples have been studied in a pharmacological experimentation aimed to the determination of the inhibitory activity of the acetylcholinesterase and the butyrylcholinesterase. The method of Ellman et al. (Ellman G.L., Courtney K. D., Andres V., Featherstone R. M.: a New and Rapid Colorimetric Determination of Acetylcholinesterase Activity, Biochem. Pharm. 7,88, 1961) has been used.

The incubation time between enzyme and product used for the determinations has been 10'.

The acetylcholinesterase from human erythrocytes (AChE hRBC), the acetylcholinesterase from Electric Eel (AChE E.eel) and the butyrylcholinesterase from human serum (BuChE hserum) coming from the Sigma Chemical have been used.

The obtained results are reported in the Table 1. In said table the results obtained by eptastigmine, physostigmine and tacrine (9-amino-1,2,3,4-tetrahydroacridine) which are known anticholinesterase substances are reported by comparison.

TABLE 1

Inhibition of the cholinesterase (IC$_{50}$ M)

| Compound | AChE E. eel | AChE hRBC | BuChE hserum |
|---|---|---|---|
| Ex. 1 | 4.7 × 10$^{-7}$ | 1.6 × 10$^{-7}$ | 1.6 × 10$^{-8}$ |
| Ex. 2 | 1.1 × 10$^{-6}$ | 4.2 × 10$^{-7}$ | 2.0 × 10$^{-8}$ |
| Ex. 3 | 1.2 × 10$^{-6}$ | 2.0 × 10$^{-7}$ | 2.0 × 10$^{-8}$ |
| Ex. 4 | 2.5 × 10$^{-7}$ | 1.3 × 10$^{-7}$ | 1.6 × 10$^{-9}$ |
| Ex. 5 | 1.2 × 10$^{-7}$ | 1.8 × 10$^{-7}$ | 3.0 × 10$^{-8}$ |
| Ex. 8 | 1.3 × 10$^{-6}$ | 2.2 × 10$^{-7}$ | 1.4 × 10$^{-8}$ |
| Ex. 12 | 1.7 × 10$^{-8}$ | 0.8 × 10$^{-7}$ | 0.5 × 10$^{-7}$ |
| Ex. 13 | 2.3 × 10$^{-8}$ | 1.5 × 10$^{-8}$ | 2.8 × 10$^{-8}$ |
| Ex. 16 | 1.4 × 10$^{-5}$ | 4.8 × 10$^{-6}$ | 0.7 × 10$^{-8}$ |
| Ex. 18 | NT | 1.0 × 10$^{-7}$ | NT |
| Ex. 19 | NT | 1.0 × 10$^{-7}$ | 2.3 × 10$^{-7}$ |
| Ex. 20 | NT | 2.2 × 10$^{-7}$ | >10$^{-4}$ |
| Ex. 21 | NT | 0.6 × 10$^{-6}$ | 0.5 × 10$^{-6}$ |
| Ex. 22 | NT | 2.1 × 10$^{-7}$ | 0.6 × 10$^{-6}$ |
| Ex. 23 | NT | 2.2 × 10$^{-7}$ | >10$^{-4}$ |
| Ex. 24 | NT | 0.6 × 10$^{-7}$ | 1.3 × 10$^{-9}$ |
| Ex. 25 | NT | 1.7 × 10$^{-6}$ | >10$^{-3}$ |
| Ex. 26 | NT | 4.0 × 10$^{-7}$ | 2.2 × 10$^{-4}$ |
| Ex. 32 | NT | 4.2 × 10$^{-7}$(*) | 7.0 × 10$^{-5}$ |
| Ex. 35 | NT | 1.3 × 10$^{-8}$(*) | >10$^{-4}$ |
| Ex. 36 | NT | 1.1 × 10$^{-6}$(*) | 2.1 × 10$^{-5}$ |
| Ex. 37 | NT | 0.6 × 10$^{-7}$(*) | 0.8 × 10$^{-5}$ |
| Ex. 38 | NT | 0.5 × 10$^{-7}$(*) | >10$^{-4}$ |
| Ex. 39 | NT | 1.1 × 10$^{-6}$(*) | >10$^{-4}$ |
| Ex. 40 | NT | 1.8 × 10$^{-7}$(*) | >10$^{-4}$ |
| Eptastigmine | 0.5 × 10$^{-7}$ | 2.9 × 10$^{-7}$ | 14.0 × 10$^{-8}$ |
| Physostigmine | 1.5 × 10$^{-7}$ | 0.5 × 10$^{-7}$ | 0.7 × 10$^{-7}$ |
| Tacrine | NT | 4.0 × 10$^{-6}$ | NT |

NT = not tested
(*) = incubation time 120'

The concentration inducing a 50% inhibition is indicated by the IC$_{50}$. The results reported in the Table 1 show that the products of the invention have a high acetylcholinesterase inhibitory activity.

Particularly active turn out the compounds of the Examples 1, 4, 5, 12, 13, 18, 19, 24, 35, 37, 38 and 40 whose potency is equal or even superior to that of eptastigmine or of physostigmine which turns out in turn superior to that of tacrine. The compounds of the Examples 20, 23, 25, 26, 35, 37, 38, 39 and 40 also show a potent and selective AChE inhibitory activity while have poor activity on the BuChE.

The compound of the Examples 1, 2, 25, 35, 38 and 40 has been estimated in comparison to eptastigmine and physostigmine for the acute toxicity (single administration) in mouse and rat.

The results are reported in Table 2.

TABLE 2

Toxicity tests (LD$_{50}$)

| | Mouse | | Rat | |
|---|---|---|---|---|
| | os | iv | os | iv |
| Ex. 1 | 67 | 15 | 33 | NT |
| Ex. 2 | >50 | NT | NT | NT |
| Ex. 25 | NT | 15 | 56 | 14 |
| Ex. 35 | NT | NT | 40 | 3 |
| Ex. 38 | NT | NT | >40 | NT |
| Ex. 40 | NT | NT | >40 | NT |
| Eptastigmine | 25 | 7 | 23 | 5 |
| Physostigmine | 3.4 | 0.6 | NT | NT |

NT = not tested

LD$_{50}$ is the dose (mg/kg) inducing 50% mortality.

The results show that the compounds of the series claimed in the present invention are provided with a low toxicity in the experimental animal. Results of other experiments also show that the compound 1, administered to rats in doses of 0.5–1–2–4 mg/kg per os, is able to reduce the amnesic failure induced by scopolamine in the Passive Avoidance test.

The values of the dosages per os used in the Passive Avoidance test, if compared with the LD$_{50}$ values, show that the claimed compounds have a high safety index.

Due to the above mentioned characteristics, the compounds of the present invention, comprising the compounds having formula (I) and their salts with pharmacologically acceptable acids, find a therapeutic application in every pathological form characterized by acetylcholine deficiency such as for example the diseases linked to memory deficit (Alzheimer Desease) or in the cerebral pathological forms of ischemic kind.

For such a purpose pharmaceutical compositions comprising effective quantities of said compounds mixed with pharmacologically acceptable diluents and excipients are prepared. Thus the invention refers also to the therapeutic method, to be applied in the human therapy in the pathologies characterized by acetylcholine deficiency, comprising oral or parenteral administration of a pharmacologically effective dose of said compounds.

The compound (I) dose to administer for the therapeutic treatment is comprised between 10 and 200 mg/die for the oral administration and between 2 and 20 mg/die for the parenteral administration.

We claim:

1. A compound of formula (I)

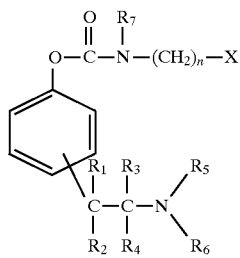

wherein $R_1, R_2, R_3$ and $R_4$, equal or different, represent: hydrogen, linear or branched ($C_1$–$C_4$) alkyl, ($C_3$–$C_6$) cycloalkyl aryl )$C_1$–$C_4$) alkyl, hydroxyl, or $R_1$ and $R_2$ together are —(CH$_2$)$_m$— wherein m is an integer number from 2 to 5 and from cycle from 3 to 6 carbon atoms;

$R_5$ and $R_6$, equal or different, represent: hydrogen, linear or branched ($C_1$–$C_6$) alkyl, aryl ($C_1$–$C_6$) alkyl, ($C_1$–$C_6$) acyl or the group:

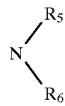

is a radical derived from the morpholine, piperidine, tetrahydroquinoline, tetrahydroisoquinoline, ($C_1$–$C_6$) alkylpiperazine, phenylpiperazine, phenyl ($C_1$–$C_6$) alkylpiperazine, ($C_1$–$C_6$) acylpiperazine, the dialkylaminoalkyl group being in para or meta position with respect to the carbamic group;

$R_7$ represents hydrogen or a linear or branched ($C_1$–$C_4$) alkyl;

n is an integer number from 0 to 20;

X represents a morpholinyl group optionally substituted on the ring carbons with halogen, $C_1$–$C_4$ alkyl or $C_1$–$C_4$ alkoxy, provided that when $R_3=R_4=H$, $R_1$ and $R_2$ cannot both be H.

2. A process of preparing a compound of formula (II)

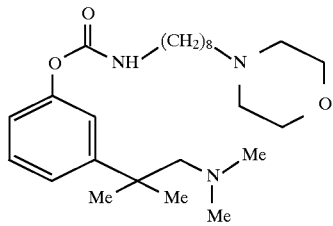
(II)

wherein

A) the compound having the formula (III)

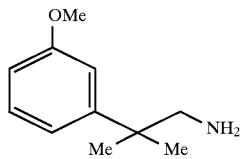
(III)

is made to react with formaldehyde in reductive amination conditions to obtain the compound (IV)

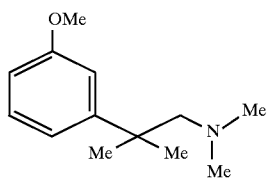
(IV)

B) the compound having formula (IV) is O-demethylated in acid conditions to obtain the compound having formula (V)

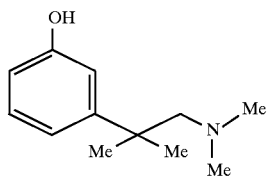
(V)

C) the compound having formula (VI)

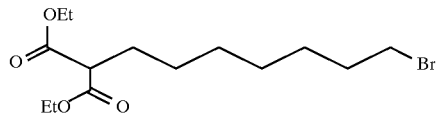
(VI)

is made to react with morpholine to obtain the compound (VII)

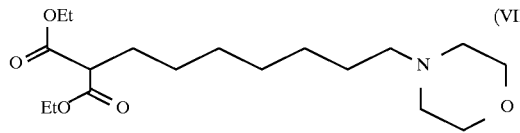
(VII)

D) the compound (VII) is monodecarboxylated to obtain the compound (VIII)

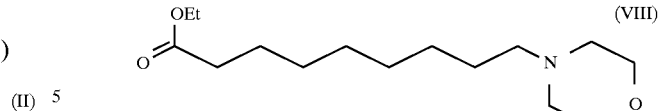
(VIII)

E) the compound (VIII) is submitted to hydroylsis, then transformed in acylazide and by Curtius rearrangement in isocynate to obtain the compound (IX)

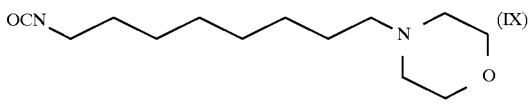
(IX)

F) the compound (V) dissolved in anhydrous toluene, is treated with metalic sodium and subsequently with the compound (IX) to obtain the desired compound (II).

3. Process as claimed in claim 2, wherein step A) comprises treating in a polar or bipolar aprotic solvent the compound (III) with formaldehyde and with a reducing agent selected between sodium borohydride and sodium cyanoborohydride with molar ratio between (III) and formaldehyde of 1:10 and with molar ratio between said reducing agent and (III) of 4:1, at a temperature between 2° and 5° C.

4. Process as claimed in claim 2, wherein step B) in an aqueous solution of HBr at 48% by weight at a temperature between the room temperature and 100° C.

5. Process as claimed in claim 2, wherein step B) is carried out by treatment with a Lewis acid selected from aluminum chloride, boron fluoride and boron tribromide in an apolar solvent selected from benzene, toluene and chlorobenzene at a temperature between 25° and 80 ° C.

6. Process as claimed in claim 2, wherein step C) is carried out in bipolar aprotic solvent selected from dimethyl formamide, dimethyl sulfoxide and acetone with a molar ratio between (VI) and morpholine between 1:2 and 1:3, at room temperature.

7. Process as claimed in claim 2, wherein step D) is carried out with a molar ratio between (VII) and boric acid between 1:1 and 1:2 at the acid melting point.

8. Process as claimed in claim 2, wherein step E) is accomplished by treatment with sodium hydroxide in boiling water, followed by the addition of acetone, of ethyl chloroformiate dissolved in acetone and of tetrabutylammonium chloride at a temperature between −5° and 0° C. and by final treatment with sodium azide dissolved in water at 0° C., the molar ratio between (VIII) and ethyl chloroformiate being comprised between 1:1 and 1:2 and the molar ratio between (VIII) and sodium azide being comprised between 1:2 and 1:3.

9. Process as claimed in claim 2, wherein step F) comprises treating of (V) with metallic sodium and with (IX) in an apolar solvent selected from benzene, xylene, chlorobenzene and toluene, at room temperature and with a molar ratio between (V) and Na comprises between 1:1 and 1:2.

10. Pharmaceutical composition for the treatment of the pathological forms derived by acetylcholine deficiency containing an effective dose of a compound having formula (I) as claimed in claim 1 as an active substance or of one of its salts, together with pharmacologically acceptable diluents or excipients.

11. Composition as claimed in claim 10 in a form suitable to oral administration.

12. Composition as claimed in claim 10 in a form suitable to the parenteral administration.

13. Therapeutic method for the treatment of the pathological forms derived by acetylcholine deficiency which comprises administering of an effective dose of a compound having formula (I) as claimed in claim 1 or of one of its pharmacologically acceptable salts.

14. The method of claim 13 wherein administration is carried out orally in a dose between 10 and 200 mg/day.

15. The method of claim 13 wherein administration is carried out parenterally in a dose between 10 and 20 m/g/day.

* * * * *